United States Patent [19]

Broadwin et al.

[11] Patent Number: 4,986,808
[45] Date of Patent: Jan. 22, 1991

[54] MAGNETOSTRICTIVE TRANSDUCER

[75] Inventors: Alan Broadwin, Brooklyn, N.Y.; Leonard M. Emery, West Haven, Conn.

[73] Assignee: Valleylab, Inc., Boulder, Colo.

[21] Appl. No.: 287,748

[22] Filed: Dec. 20, 1988

[51] Int. Cl.⁵ .............................................. A61M 1/00
[52] U.S. Cl. ................................. 604/22; 128/24 A; 310/26; 366/127
[58] Field of Search ...................... 128/24 A; 604/22; 366/127; 310/26; 51/59 SS

[56]  References Cited

U.S. PATENT DOCUMENTS

| 2,826,396 | 3/1955 | Murdoch, Jr. | 366/127 |
| 3,311,352 | 3/1967 | Dostal | 310/26 |
| 3,370,186 | 2/1968 | Antonevich | 336/127 |
| 3,375,583 | 4/1968 | Blank et al. | 128/24 A |
| 4,330,278 | 5/1982 | Martin | 128/24 A |
| 4,425,115 | 1/1984 | Wuchinich | 604/22 |

FOREIGN PATENT DOCUMENTS 855917 7/1949 Fed. Rep. of Germany ........ 310/26

Primary Examiner—William E. Kamm
Assistant Examiner—Krista M. Pfaffle
Attorney, Agent, or Firm—Peter C. Richardson; Lawrence C. Akers; Mark Dryer

[57] ABSTRACT

A magnetostrictive transducer comprising a plurality of elongated strips of magnetostrictive material, each strip having a proximal end, a distal end and a substantially V-shaped cross section wherein each arm of the V is formed by a longitudinal length of the strip, each strip being attached to an adjacent strip at both the proximal end and the distal end to form and integral substantially rigid column having a central axis with fins extending radially relative to said axis; and an ultrasonic resonant vibrator including such a transducer.

5 Claims, 1 Drawing Sheet

MAGNETOSTRICTIVE TRANSDUCER

BACKGROUND OF THE INVENTION

This invention relates to a magnetostrictive transducer, particularly to a magnetostrictive transducer of improved configuration for use in an ultrasonic resonant vibrator, more particularly to an ultrasonic resonant vibrator in a surgical handpiece.

Apparatus incorporating an ultrasonic resonant vibrator is known in the art for surgical use, particularly for surgical handpieces comprising tools for fragmenting tissue. In such apparatus the required ultrasonic vibrations may be produced by magnetostrictive means transmitted through a connecting member to an appropriate tool.

A representative example of such an apparatus is disclosed in U.S. Pat. No. 4,223,676, the disclosure of which is incorporated herein by reference. In the apparatus disclosed in U.S. Pat. No. 4,223,676 the magnetostrictive transducer is a magnetostrictive stack composed of a nickel alloy sandwich such as is taught in U.S. Pat. No. RE 25,033. The said stack comprises a plurality of elongated strips of magnetostrictive material, i.e. nickel alloy, forming a laminated structure. The laminations are necessary to reduce adverse effects, e.g. energy loss, from eddy currents.

In a later improved design the laminated stack was made with a shallow curved profile for added rigidity.

In order to function properly, a laminated transducer preferably:

1. should be mechanically stiff;
2. have minimum acoustic losses; and
3. should be relatively easy to handle away from its operating environment.

The transducer described above has proved to be effective and highly serviceable in its use in surgical procedures. However, despite its good performance record, it still has certain disadvantages. For example, the flat laminated structure tends to overheat if the flow of coolant is reduced for any reason and such overheating may result in serious damage to the apparatus. Also the flat construction gives mechanical stiffness in only one plane. This lack of overall rigidity may result in mechanical damage due to mishandling and, if the laminations become separated or bent, the entire apparatus may be rendered useless.

It has now been found that the above disadvantages are overcome if the transducer is made in the form of a substantially rigid column comprising elongated strips arranged in the form of radially extending fins.

SUMMARY OF THE INVENTION

In accordance with the invention there is provided a magnetostrictive transducer comprising a plurality of elongated strips of magnetostrictive material, each strip having a proximal end, a distal end and a substantially V-shaped cross section wherein each arm of the V is formed by the longitudinal length of the strip, each strip being attached to an adjacent strip at both the proximal end and the distal end to form an integral substantially rigid column having a central axis with fins extending radially relative to said axis.

Preferably, the attachment of the ends of each strip to the ends of each adjacent strip is made by brazing or welding.

A particularly preferred embodiment of the invention is a transducer as described above in which each arm of each V-shaped strip is in touching contact with an arm of an immediately adjacent strip along the complete longitudinal length of the strip to form a radially extending fin and the resulting fins form a radial pattern around a central hole extending the length of the resulting substantially rigid column.

The invention also provides an ultrasonic resonant vibrator which comprises an ultrasonic transducer, a surgical tool and connecting portion which connects said tool transducer to said tool, wherein said transducer is a magnetostrictive transducer as described above.

Preferably, said magnetostrictive transducer has a central hole extending along its length, which hole accommodates a tube for transporting fluid.

DETAILED DESCRIPTION OF THE INVENTION

In contrast to the conventional laminated stack of the prior art, the transducer of the present invention is in the form of a substantially rigid column, preferably of substantially circular cross section, having a central axis and fins extending radially relative to said axis. Said fins are formed by elongated strips of magnetostrictive material, for example a nickel alloy having a suitable oxide coating, attached to each other at their distal and proximal ends, preferably by brazing or welding. In a preferred embodiment, each of the elongated strips is of substantially V-shaped cross section and the said column is formed by aligning each strip so that one of the arms thereof is in touching contact with an arm of the immediately adjacent strip along its complete longitudinal length so that the touching strips form a radial pattern of fins around a central hole extending the length of the column. The resulting structure is a substantially rigid column which is stiffer than the laminated stack of the prior art and moreover the fin arrangement provides a plurality of free surfaces which facilitate radiative heat loss and thereby reduce the possibility of overheating if the normal cooling means should fail.

Although the V-shaped cross section is particularly preferred for the longitudinal strips, strips of any other suitable cross section may be used. The V-shape is particularly suitable because of ease of fabrication of the individual strips and simplicity of construction of the columnar configuration using a plurality of such strips. Depending upon the number of strips used and the closeness of the packing, the column formed when the strips are attached to each other at their ends will usually have a central hole extending along its length, and, if desired, the diameter of said hole may be made large enough to accommodate a tube for transporting aspiration or irrigation fluid.

The preferred transducer according to the invention is particularly adapted to be used in a surgical handpiece comprising an ultrasonic resonant vibrator which includes a surgical tool connected through a connecting portion to an ultrasonic vibration transducer. In such apparatus one end of the magnetostrictive transducer of the invention is connected to the proximal end of a connecting portion, which amplifies the ultrasonic vibration, and the distal end of said connecting portion is attached to the proximal end of a surgical tool. The configuration and mass of the surgical tool is such that further amplification is obtained which makes the tool suitable, for example, for the fragmentation of tissue. A typical surgical handpiece is disclosed in Pat. No. 4,223,676.

DESCRIPTION OF THE DRAWINGS

The invention will be more particularly described with reference to a prior art transducer and a preferred embodiment of the present invention as illustrated in the accompanying drawings, in which:

Referring to FIGS. 1-3 of the drawings, a typical prior art laminated stack 10 comprises a plurality of substantially flat strips 11 stacked in side by side relationship and attached at their ends by connecting pieces 12, 13. As illustrated in FIG. 2 a shallow curved profile may be impressed into the otherwise flat strips to enhance the rigidity of the stack. The laminated transducer is adapted to be connected to a suitable connecting portion by an appropriate threaded connector 14 or other suitable attaching device.

Figure 1:
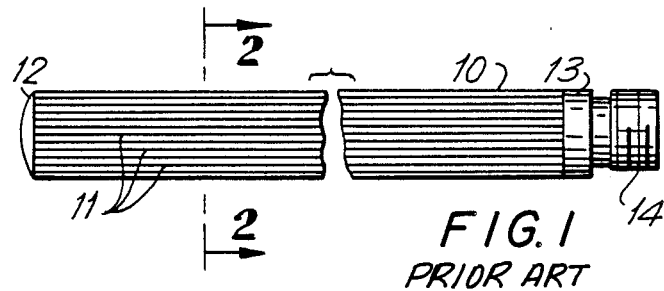
FIG. 1 is a side elevation of a laminated stack as disclosed in the prior art.
Figure 2:
FIG. 2 is a cross section through line 2—2 of FIG. 1.
Figure 3:
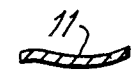
FIG. 3 is an enlarged cross section of a single strip of the prior art stack.
Figure 4:
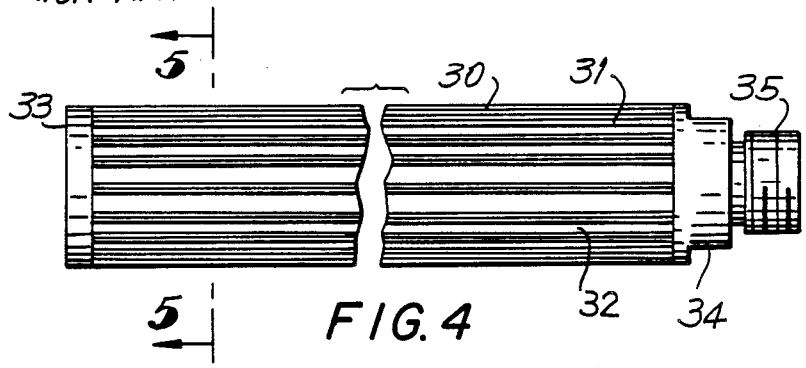
FIG. 4 is a side elevation of a finned transducer according to the present invention.
Figure 5:
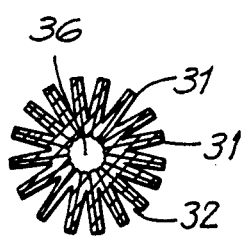
FIG. 5 is a cross section through line 5—5 of FIG. 4.
Figure 6:
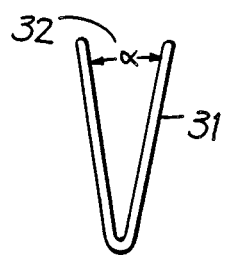
FIG. 6 is an enlarged cross section of a V-shaped elongated strip used in the transducer of FIG. 4.

A preferred embodiment of the invention is illustrated in FIGS 4-6. This embodiment comprises a column 30 formed from a plurality, for example sixteen to thirty-five, preferably eighteen, of elongated strips of magnetostrictive material, each having a substantially V-shaped cross section. The magnetostrictive material is preferably a nickel alloy with an oxide coating.

Each of the arms 31 of each V is in touching contact with an arm of the V-shaped adjacent strip. Typically the space 32 between said arms is defined by an angle $\alpha$, which preferably is from 11° to 21°. The length of each of the elongated strips is determined by the wavelength of the current used in the magnetostrictive source. Thus the length of the transducer has to be equivalent to an integral number of half wavelengths so that the center thereof is located at a nodal point. For a resonant vibrator which operates at a frequency of about 22 to 27 KHz, the length of the transducer, and hence the length of each of the strips from which it is composed will be about 4 inches (about 10 cm.).

The thickness of each strip is about 0.007 to 0.010 inch (0.018 to 0.025 cm.).

The elongated strips are attached to each other at their proximal end 33 and distal end 34. The attachment is preferably made by brazing or welding. Although illustrated schematically as a solid piece at each end, the attachment may be either a solid piece, as shown, or an open structure formed by a bond between each adjacent strip end, provided the resulting column possesses the desired rigidity and stiffness.

Attached to the distal end of the column is a suitable connector 35 for connecting the transducer to other driven members, for example the connecting portion to which is further attached a surgical tool as described hereinabove.

Figure 7:
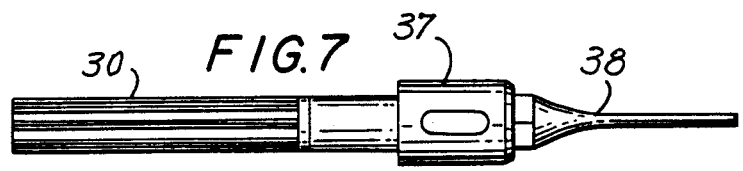
FIG. 7 is a side elevation of an ultrasonic resonant vibrator incorporating a transducer of the invention.

FIG. 7 illustrates schematically an ultrasonic resonant vibrator comprising a transducer 30 according to the invention connected to a connecting portion 37 and a surgical tool 38.

As shown in FIG. 5 the preferred embodiment may contain a central hole 36. The diameter of this hole may be varied so as to accommodate other operating members of the apparatus, for example a tube for transporting aspiration or irrigation fluid.

The embodiment illustrated in FIGS 4-6 of the drawings possesses a greater rigidity and stiffness than any laminated transducer known in the prior art and additionally possesses a configuration which reduces or completely avoids the overheating problems associated with the prior art devices. Thus, in a test wherein a surgical handpiece containing a transducer according to the invention was run for 5 to 7 minutes without cooling, upon removal of the transducer, it was found to be warm, but not as hot as a conventional stack without cooling.

Furthermore, it was found that a handpiece containing a transducer according to the invention required less operating power, indicating that the transducer of the invention is more efficient than conventional prior art transducer stacks.

We claim:

1. A magnetostrictive transducer comprising a plurality of elongated strips of magnetostrictive material, each of said strips having a proximal end, a distal end and a substantially V-shaped cross section wherein each arm of the V-shaped cross section is formed by the longitudinal length of each of said strips, each arm of each of said strips being attached along the radial length of each arm to each arm of each adjacent one of said strips only at both the proximal end and the distal end to form an integral substantially rigid column having a central axis with fins extending radially relative to said axis.

2. A transducer according to claim 1, in which the attachment of the ends of each of said strips to the ends of each of said adjacent strips is made by brazing or welding.

3. A transducer according to claim 1, in which each said arm of each of said strips is in touching contact with an arm of an immediately said adjacent one of said strips along the complete longitudinal length of the strip to form a radially extending fin which fin is one of a plurality of fins resulting from said plurality of elongated strips which form a radial pattern around a central hole extending the length of the substantially rigid column.

4. An ultrasonic resonant vibrator which comprises an ultrasonic transducer, a surgical tool and a connecting portion which connects said transducer to said tool, wherein said transducer is a magnetostrictive transducer comprising a plurality of elongated strips of magnetostrictive material, each of said strips having a proximal end, a distal end and a substantially V-shaped cross section wherein each arm of the V-shaped cross section is formed by the longitudinal length of each of said strips, each arm of each one of said strips being attached along the radial length of each arm to each arm of each adjacent one of said strips only at both the proximal end and the distal end to form an integral substantially rigid column having a central axis with fins extending radially relative to said axis.

5. A vibrator according to claim 4, in which said magnetostrictive transducer has a central hole extending along the length of said central axis and a tube for transporting fluid accommodated through said hole.

* * * * *